(12) United States Patent
Pero

(10) Patent No.: US 6,964,784 B2
(45) Date of Patent: Nov. 15, 2005

(54) METHOD OF PREPARATION AND COMPOSITION OF A WATER SOLUBLE EXTRACT OF THE BIOACTIVE COMPONENT OF THE PLANT SPECIES UNCARIA FOR ENHANCING IMMUNE, ANTI-INFLAMMATORY, ANTI-TUMOR AND DNA REPAIR PROCESSES OF WARM BLOODED ANIMALS

(75) Inventor: Ronald W. Pero, Arlington, VT (US)

(73) Assignee: Optigenex, Inc., New York, NY (US)

( * ) Notice: Subject to any disclaimer, the term of this patent is extended or adjusted under 35 U.S.C. 154(b) by 0 days.

(21) Appl. No.: 10/093,794

(22) Filed: Mar. 7, 2002

(65) Prior Publication Data

US 2003/0170320 A1 Sep. 11, 2003

(51) Int. Cl.$^7$ .................... A61K 35/78; A61K 31/34; A61K 31/05
(52) U.S. Cl. .................. 424/725; 514/470; 514/731; 514/732
(58) Field of Search ............... 424/725; 514/470, 514/731, 732

(56) References Cited

U.S. PATENT DOCUMENTS

| 4,363,815 A | * | 12/1982 | Yu et al. ............. 514/263.31 |
| 4,940,803 A | * | 7/1990 | Mills et al. ............. 549/302 |
| 5,401,858 A | * | 3/1995 | Huynh-Ba ............. 549/302 |
| 6,039,949 A | * | 3/2000 | Pero ............. 424/769 |
| 6,238,675 B1 | * | 5/2001 | Pero ............. 424/775 |
| 2003/0013758 A1 | * | 1/2003 | Paulis et al. ............. 514/470 |

FOREIGN PATENT DOCUMENTS

| DE | 1095821 | * | 8/1963 |
| DE | 1905875 | * | 8/1970 |
| EP | 343723 | * | 11/1989 |
| JP | 11245503 | * | 9/1999 |

OTHER PUBLICATIONS

Suzuki et al Green Coffee Bean Extract and its Metabolites Have a Hypotensive Effect . . . Hypertension Research, Clinical and Experimental, Osaka Vo. 25. No. 1, 2002 pp 99–107.

Anna Capasso et al "Phytochemical and Pharmacological Studies of *Guettarda acreana*", Plana Medica vol. 64, No. 4, May 1998 pp 348–352.

* cited by examiner

Primary Examiner—Christopher R. Tate
(74) Attorney, Agent, or Firm—Gibbons, Del Deo, Dolan, Griffinger & Vecchione

(57) ABSTRACT

A method for isolating the bioactive component of the water-soluble extract of *Uncaria tomentosa* known as C-MED-100®, comprising (i) precipitating the spray drying carrier from C-MED-100®; (ii) using the resulting C-MED-100® to obtain a spotting mixture for thin layer chromatography (TLC); (iii) spotting the C-MED-100® spotting mixture on pre-run TLC plates and eluting the plates to obtain the fluorescing band with $R_f$=0.2–0.3; (iv) scraping off the $R_f$=0.2–0.3 band, eluting it in ammonia and freeze drying the eluted band to form a powder; and (v) extracting the powder with methanol to remove solubilized silica gel, concentrating the methanol solution and crystalizing the concentrated solution to obtain the bioactive component. The isolated bioactive component is a quinic acid analog, preferably quinic acid lactone. A pharmaceutical composition comprising a pharmaceutically effective amount of the bioactive component and a nontoxic inert carrier or diluent. The bioactive component may be used to enhance immune competency, treat disorders associated with the immune system, inhibit the inflammatory response, treat disorders associated with the inflammatory response, enhance the anti-tumor response, and treat disorders associated with the response to tumor formation and growth, all in mammals.

8 Claims, 1 Drawing Sheet

METHOD OF PREPARATION AND COMPOSITION OF A WATER SOLUBLE EXTRACT OF THE BIOACTIVE COMPONENT OF THE PLANT SPECIES UNCARIA FOR ENHANCING IMMUNE, ANTI-INFLAMMATORY, ANTI-TUMOR AND DNA REPAIR PROCESSES OF WARM BLOODED ANIMALS

CROSS-REFERENCE TO RELATED APPLICATIONS

None.

STATEMENT REGARDING FEDERALLY SPONSORED RESEARCH OR DEVELOPMENT

None.

REFERENCE TO SEQUENCE LISTING

None.

BACKGROUND OF THE INVENTION

1. Field of the Invention

The present invention is directed to the isolation, purification and structural identification of the bioactive component of water extracts of Cat's Claw (*Uncaria* species). The bioactive component is identified as quinic acid lactone. The present invention also is directed to the pharmaceutical use of said bioactive component for enhancing the immune, anti-inflammatory, anti-aging, anti-tumor and DNA repair processes in warm blooded animals.

2. Discussion of the Related Art

*Uncaria tomentosa*, commonly known as Una de Gato or Cat's Claw, has been widely used historically as a natural remedy, and is currently present in a number of nutritional formulations to treat a large variety of health disorders. To applicant's knowledge, all of the commercial preparations of Cat's Claw except the water soluble extract (the "Pero extract") disclosed in U.S. Pat. Nos. 6,039,949 and 6,238,675 B1 and allowed patent U.S. Ser. No. 09/824,508 (the "Pero patents") to Pero are based on the oxindole alkaloid content thereof. This is due to Dr. Keplinger's (Austria) discovery, in the early 1960's, of the presence of oxindole alkaloids. (Keplinger, K., Laus, G., Wurm, M., Dierich, M. P., Teppner, H. *Uncaria tomentosa* (Willd.) DC.- Ethnomedicinal use and new pharmacological, toxicological and botanical results, J. Ethanopharmacology 64:23–34, 1999). The Pero extract, the preferred embodiment of which is commercially available under the name C-MED-100®, is a novel Cat's Claw extract quite unlike any other commercial versions in that it contains only traces of alkaloids (<0.05%). Instead, the Pero extract contains a new class of active ingredients, carboxyl alkyl esters (CAEs), having demonstrated efficacy as described and protected in the Pero patents. C-MED-100® is the first product offered in the nutritional industry to support both auto-immune and DNA repair-ehnancing functions, which are of critical importance in reducing the consequences of age-related disorders such as autoimmune, inflammatory and neoplastic diseases. References herein to C-MED-100® shall be understood to include the Pero extract, of which C-MED-100® is a preferred embodiment.

The precise chemical identification of the Pero extract's active ingredients has not heretofore been achieved. However, the chemical and biological characteristics of those ingredients have been sufficiently completed to standardize the commercial manufacture of the Pero extract. (See the Pero patents).

C-MED-100®, which is the commercially available Pero extract, is formulated and based on the historical medicinal uses of Cat's Claw, of which an important step is exhaustive hot water extraction for approximately 18 hours at around 95° C. The extract is then ultrafiltrated to remove high molecular weight (>10,000 MW) toxic conjugates, and spray dried to contain 8–10% carboxy alkyl esters (CAEs) as active ingredients. CAEs were characterized as the only active ingredients of C-MED-100® as a result of their absorption (85%) onto charcoal. No biological activity was observed in the unabsorbed fraction. Using thin layer chromatography (TLC) as the purification tool, the active ingredients showed a UV absorption maximum at about 200 $\mu$nm, and reacted with hydroxylamine and ferric chloride, thus characterizing them as esters (e.g. CAEs).

Daily oral doses of C-MED-100® between 250–700 mg have proven efficacious in humans. These dosages have been shown to enhance anti-inflammatory, DNA repair, immuno and anti-tumor processes of warm blooded animals, including humans. (See the Pero patents, Lamm, S., Sheng, Y., Pero, R. W., Persistent response to pneumococcal vaccine in individuals supplemented with a novel water soluble extract of *Uncaria tomentosa*, C-Med-100. Phytomed 8: 267–274, 2001; Sheng, Y., Li, L., Holmgren, K., Pero, R. W., DNA repair enhancement of aqueous extracts of *Uncaria Tomentosa* in a human volunteer study. Phytomed 8: 275–282, 2001; Sheng, Y., Bryngelsson, C., Pero, R. W. Enhanced DNA repair, immune function and reduced toxicity of C-MED-100™, a novel aqueous extract from *Uncaria tomentosa*. J. of Ethnopharmacology 69:115–126 (2000)).

The CAEs in C-MED-100® are shown to give profound nutritional support as a dietary supplement because the CAEs enhance both DNA repair and immune cell responses, which, in turn, are the critical physiological processes that regulate aging. (See the Pero patents, Sheng, Y., Pero, R. W., Wagner, H., Treatment of chemotherapy-induced leukopenia in a rat model with aqueous extract from *Uncaria tomentosa*. Phytomedicine 7(2):137–143 (2000) and as cited above). Both of these processes involve regulating the nuclear transcription kappa beta (NF-kB). NF-kB is well known to control (i) the nuclear events that salvage cells from apoptotic cell death and (ii) pro-inflammatory cytokine production. (Beg, AA and Baltimore, D., An essential role for NF-kB in preventing TNF-α induced cell death. Science 274: 782–784, 1996; Wang, C-Y, Mayo, M. W., Baldwin, A. S., TNF-α and cancer therapy-induced apoptosis: Potentiation by inhibition of NF-kB. Science 274: 784–787, 1996). Hence, this mechanism directly connects induction of apoptosis to programmed cell toxicity with inhibition of pro-inflammatory cytokine production and inflammation.

Apoptosis is an essential biochemical process in the body that regulates cells from division (replication) into differentiation and toward an increased functional capacity. Cells entering apoptosis will not only be stimulated to differentiate and increase functionality but will eventually die from this "programmed cell death". Thus, induced apoptosis resulting from NF-kB inhibition by C-MED-100® would (i) effectively kill tumor cells, because they would be forced out of replication by apoptosis and into eventual death; and simultaneously (ii) increase immune cell responsiveness, because more immune competent cells would be forced to differentiate and would live longer because of the parallel enhancement of DNA repair.

NF-kB also sends signals to inflammatory cells instructing them to produce cytokines (growth factors). These signals, in turn, stimulate phagocytic cells to kill more invading infectious agents, which, at least in part, is accomplished by producing high levels of oxygen free radicals. Thus, inhibiting NF-kB has anti-inflammatory properties because it prevents over-reaction of the inflammatory process that can be harmful to normal body tissues. In addition, because pro-inflammatory cytokines are a major source of endogenous free radical production in humans, NF-kB inhibition is antimutagenic by reducing genetic damage that may accumulate over the years. As fewer radicals are produced, there is less damage to the DNA and less inhibition of natural repair. A result is that aging is curtailed.

The Pero extract, preferably C-MED-100®, is thus an ultimate nutritional supplement for anti-aging remedies because it prevents free radical damage by NF-kB inhibition, induces differentiation and immune cell responsiveness by apoptosis, enhances DNA repair, and kills tumor cells, which in turn are the major factors related to aging. (Sheng, Y., Pero, R. W., Amiri, A. and Bryngelsson, C. Induction of apoptosis and inhibition of proliferation and clonogenic growth of human leukemic cell lines treated with aqueous extracts of Uncaria Tomentosa. Anticancer Research 18:3363–3368(1998); Sandoval-Chacon M, Thompson J H, Zhang X J, Liu X, Mannick E E, Sadowicka H, Charbonet R M, Clark D A, Miller M J. Anti-inflammatory actions of cat's claw: the role of NF-kappa B. Aliment Pharmacol Ther 12: 1279–1289, 1998; Sandoval M, Charbonnet R M, Okuhama N N, Roberts J, Krenova Z, Trentacosti, A M, Miller M J. Cat's claw inhibits TNF alpha production and scavenges free radicals: role in cytoprotection. Free Radicals Biol. Med. 29(1): 71–78, 2000). It is beneficial to identify the active component thereof. By isolating and identifying the active component, it is possible to purify the component and enhance the pharmaceutical use and increase the efficacy thereof.

The present invention is directed to the isolation, purification and identification of the CAEs characterized as the active ingredients of the Pero extract, which CAEs are identified and structurally elucidated as quinic acid analogs.

BRIEF SUMMARY OF THE INVENTION

If the plant species Uncaria is hot water extracted, which has been the historical practice for medicinal use, and then ultrafiltrated to deplete large molecular weight (>10,000) components, including, for example, toxic conjugates of tannins, there still remains in the non-ultrafiltrated fraction, a novel phytomedicinal preparation of Uncaria (e.g. C-MED-100®) having potent immuno, anti-tumor, anti-inflammatory, and DNA repair enhancing properties. In a preferred embodiment of the present invention, C-MED-100® is dissolved in water, spray dried and the spray drying agent (starch) removed by precipitation with 90% aqueous ethanol. The resultant solution is subjected to thin layer chromatography (TLC) on silica gel to identify the active ingredient(s) giving the product its efficacy. The 90% ethanol C-MED-100® is spotted on (applied to) TLC plates (silica gel 60 $F_{254}$) and then chromatographed in a system of approximately 1% ammonia in greater than about 95% ethanol. There is only one area on the TLC chromatogram having biological activity (at $R_f$=0.2–0.3) when eluted with 1% aqueous ammonia and subsequently bioassayed for the ability to kill tumor cells by induction of apoptosis. The $R_f$=0.2–0.3 compound shows an ultraviolet absorption maximum in water at about 200 nm, absorbs onto charcoal and is characterized chemically as a CAE by reaction with hydroxyl amine and ferric chloride. (Bartos, Colorimetric determination of organic compounds by formation of hydroxamic acids, Talanta 27: 583–590, 1980).

In another embodiment of this invention, the biologically active CAEs isolated from the Pero extract, preferably C-MED-100®, are further purified and structurally identified as a quinic acid analog. Elution from silica TLC plates with aqueous ammonia proved to be necessary because of very tight binding to silica. Although the $R_f$=0.2–0.3 spot is essentially free from other C-MED-100® components, it contains relative large amounts of dissolved inorganic silica. In order to remove the inorganic component(s) introduced from the purification scheme on silica TLC, the 1% aqueous ammonia solution is freeze dried and then re-dissolved in methanol, leaving behind the solubilized silica. The $R_f$=0.2–0.3 spot is crystalized from methanol and subsequently identified by chemical analysis as quinic acid.

Thus, one embodiment of the present invention comprises a method for isolating the bioactive component of the Pero extract, preferably C-MED-100®, comprising: (a) precipitating the spray drying carrier from the Pero extract by mixing the extract with distilled water and evaporating the ethanol, and freeze drying the water-dissolved extract; (b) mixing the freeze-dried extract with distilled water and ethanol to obtain a spotting mixture for thin layer chromatography; (c) spotting the mixture on pre-run TLC plates and chromatographing the plates in a system of approximately 1% ammonia and ethanol, thereby obtaining a fluorescing band with $R_f$=0.2–0.3; (d) scraping off the fluorescing band with $R_f$=0.2–0.3; (e) eluting the scraped band with aqueous ammonia and freeze drying the eluted scraped band to dryness to form a powder; (f) extracting the powder with methanol to remove solubilized silica gel, leaving a methanol solution; (g) concentrating the methanol solution; and (h) crystalizing the concentrated solution to obtain the bioactive component.

Another embodiment of the present invention comprises identification of the bioactive component of the Pero extract, preferably C-MED-100®, obtained by the foregoing method. In this embodiment the bioactive component exhibits the same properties as the Pero extract and consists essentially of a quinic acid analog. Preferably, the quinic acid analog is quinic acid lactone.

In another embodiment, the present invention comprises a pharmaceutical composition comprising a pharmaceutically effective amount of the bioactive component of the Pero extract and a nontoxic inert carrier or diluent. The present invention also includes embodiments which comprise using the pharmaceutical composition to (i) enhance the immune competency of a mammal by inhibiting TNF-α production or inducing apoptosis of white blood cells, comprising administering the pharmaceutical composition in an amount effective to inhibit TNF-α production or to induce apoptosis of white blood cells; (ii) treat disorders associated with the immune system of a mammal by inhibiting TNF-α production or inducing apoptosis of white blood cells, comprising administering the pharmaceutical composition in an amount effective to inhibit TNF-α production or to induce apoptosis of white blood cells; (iii) inhibit the inflammatory response of a mammal by inhibiting TNF-α production or inducing apoptosis of white blood cells, comprising administering the pharmaceutical composition in an amount effective to inhibit TNF-α production or to induce apoptosis of white blood cells; (iv) treat disorders associated with the inflammatory response of a mammal by inhibiting TNF-α production or inducing apoptosis of white blood cells, comprising administering the pharmaceutical composition in an amount effective to inhibit TNF-α production or to induce apoptosis of white blood cells; (v) enhance the anti-tumor response of a mammal by inducing apoptosis of tumor cells, comprising administering the pharmaceutical composition in an amount effective to induce apoptosis of tumor cells; (vi) treat disorders associated with the response of a mammal to tumor formation and growth by inducing apoptosis of tumor cells, comprising administering the pharmaceutical composition in an amount effective to induce apoptosis of tumor cells; and (vii) enhance the DNA repair processes of a mammal, and, thus, provide anti-mutagenic activity important to treating aging disorders.

DETAILED DESCRIPTION OF THE INVENTION

Figure 1:
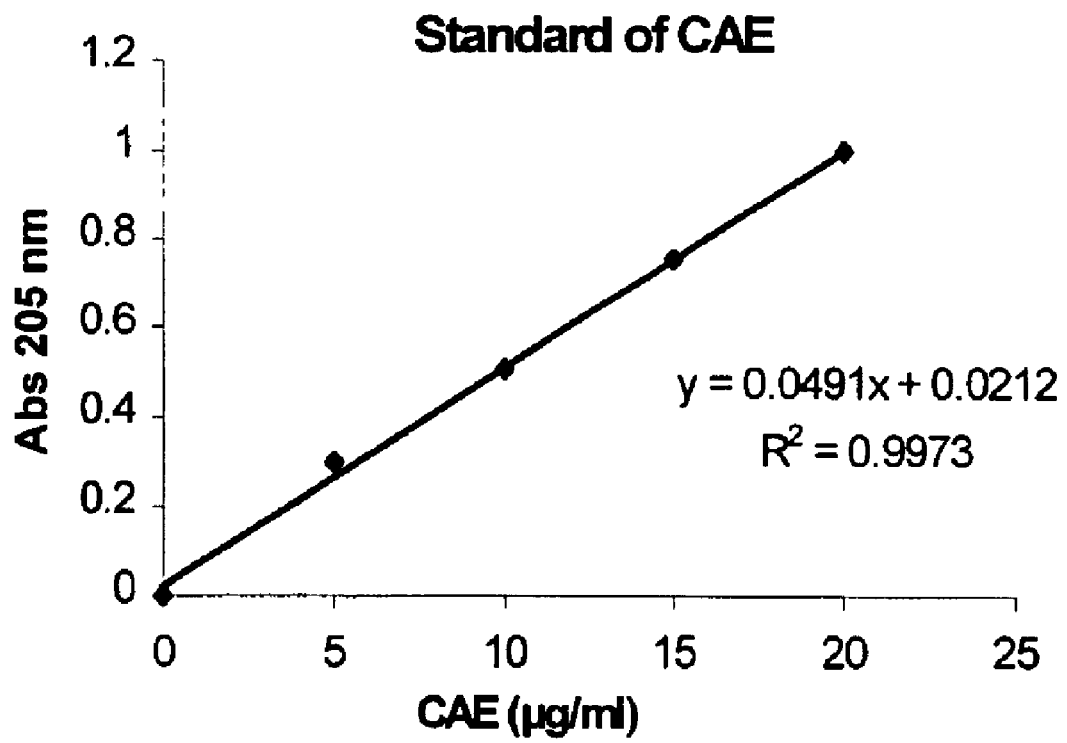
FIG. 1 shows the linear regression of UV absorbence versus CAE (estimated as __g/ml using dioctyl phthalate as standard).

The method and composition of the present invention are best understood with reference to the following examples:

EXAMPLE 1

Isolation and Purification of the Bioactive Component of the Pero extract. The method of preparation and the composition of the Pero extract, preferably C-MED-100®, are described in the Pero patents which are incorporated herein by reference. C-MED-100®, a preferred embodiment of the Pero extract, is a hot water extraction of Cat's Claw (*Uncaria tomentosa*) carried out for 18–24 hours at 90–100° C. and ultra-filtrated to remove compounds greater than 10,000 molecular weight as previously described in the Pero patents. C-MED-100® is further prepared for the commercial market by spray drying the extract with corn starch (Niro F-10 Spray-Drier). Procedures are currently used to purify the active components of C-MED-100® as CAEs and it is understood that these procedures would apply to any Pero extract. The procedures are:

1. C-MED-100® work-up for active ingredient estimation: The CAEs in C-MED-100® have very unusual water solubility. They tend to bind to tannin and polysaccharide polymers, and so, when dried, are difficult to redissolve in appropriate organic solvents such as ethanol. The preferred procedure, and it should be understood that the parameters provided are approximations and not strict limitations, is:

(a) 100 mg of C-MED-100® is dissolved in 1 ml distilled water in a glass tube for 30 minutes. The dissolved solution is centrifuged at 2000×g for 10 minutes. The resulting first supernatant is reserved for analysis.

(b) 200 µl of the first supernatant is placed into a new glass tube, and 4.8 ml of 99.7% ethanol is added thereto. The resulting solution contains 4 mg/ml C-MED-100® suspended in about 96% ethanol.

(c) The C-MED-100® ethanol solution is vortexed (mixed) and centrifuged at 2000×g to remove insoluble material. The resulting second supernatant is reserved for analysis.

(d) The second supernatant is diluted from a C-MED-100® concentration of 4 mg/ml to one of 30–200 µg/ml with 99.7% ethanol for measurement of UV absorbence. Preferably, concentrations of 60 and 120 µg/ml are examined as duplicate concentrations for calculation of CAE by UV absorbence.

(e) The UV absorbence at 205 nm for the two concentrations of C-MED-100® (preferably 60 and 120 µg/ml) is measured in a UV spectrophotometer. Because the CAEs in C-MED-100® have a UV maximum absorption at 205 nm, the amount of CAE may be estimated by the degree of UV absorption. The standard curve showing the amount of CAE in g/ml in relation to the degree of UV absorption is shown in FIG. 1.

(f) Calculation of the concentration of CAEs, in µg/ml, is determined by linear regression analysis of the slope of best fit by the equation y=0.049×+0.212, where y=UV absorbence values determined and x=concentration of CAE (µg/ml). The two different concentrations of C-MED-100 ((preferably 60 and 120 µg/ml) then serve as the denominator for which the calculated CAE from the UV standard curve serves as the nominator in the calculation of percentage CAE in C-MED-100®. In practice, the two values are averaged.

(g) The foregoing procedure has been validated against a colorimetric procedure involving conversion of CAE to hydroxamic acids and reaction with ferric chloride. (Bartos, Colorimetric determination of organic compounds by formation of hydroxamic acids, Telanta 27: 583–590, 1980). The two procedures give the same estimation of CAE content.

2. Analytical procedures for final purification and isolation of C-MED-100®'s active ingredient. Again, the parameters provided are approximations and should serve as exemplary not as limitations:

(i) Precipitation of spray drying carrier (corn starch) from crude water extracts of C-MED-100®: 5 g of C-MED-100® is mixed with 50 ml distilled water and 950 ml 99.7% ethanol. The ethanol is evaporated off in the air and the resulting solution is freeze dried. Yield is approximately 1 g.

(ii) Silica gel thin layer chromatography (TLC) purification and isolation of C-MED-100®'s active ingredient:

Step 1: To 200 mg C-MED-100® minus the removal of starch (after procedure no. 1 above), add 200 µl distilled water and 200 µl 95.5% ethanol. Mix to form a spotting mixture.

Step 2: Spot the spotting mixture of Step 1 on 4 pre-run TLC plates (Silica gel 60$F_{254}$). The elution system consists of approximately 1% $NH_3$ in at least 95% ethanol. The sole active component is found at $R_f$=0.2–0.3.

Step 3: Scrape off the fluorescing blue band with $R_f$=0.2–0.3. Eluate with approximately 1% aqueous ammonia and freeze dry to dryness.

Step 4: Extract the powder from Step 3 with methanol to remove solubilized silica gel. Concentrate the methanol solution and crystalize the active component.

(iii) High pressure liquid chromatography (HPLC) quantitative determination of active component: The column preferably is a 3 µm $C_{18}$ column (83 mm×4.3 mm internal diameter, Perkin Elmer Corp., Norwalk, Conn.). The preferred solvent gradient elution is as follows: Pump B contains methanol and pump A contains 1% acetic acid in distilled water. A gradient was run from 10% to 90% over a period of 25 minutes at a flow rate at 1.5 ml/min. Detection is at UV 254 nm. The peak appears at 18 minutes into the gradient run.

(iv) Spectrophotometric detection of active ingredients: The active component of C-MED-100(has an absorption maximum in water in the UV range at about 200 nm. Hence, crude extracts of C-MED-100® also having an absorption maximum at about 200 nm as well as its purified active components such as CAEs and their corresponding organic acids can be estimated by UV absorption at this wavelength against a known CAE standard.

An assay of biological activity of C-MED-100®'s active ingredient is prepared as follows: HL-60 W6899 cells are exposed in microculture at 5000 cells per well (96-well plates) for 5 days at 37° C. in a $CO_2$ incubator. After incubation, the cells are washed with saline and clonogenicity estimated by MTT assay. Results of the assay are summarized in Table 1, below.

EXAMPLE 2

Analytical identification of the active ingredient of C-MED-100® as quinic acid. The bioactive component (sample approximately 1 mg) isolated by TLC is completely dissolved in about 0.7 ml $D_2O$ for NMR with no shift reagent added. The following spectra are recorded:

| NMR 020108ta | |
| --- | --- |
| -1: | $^1H$ |
| -2: | $^1H/^1H$-correlated spectra; COSY |
| -3: | $^1H/^{13}C$-correlated spectra; HMBC. |
| -4: | $^{13}C$-Dept135. |
| -5: | $^1H/^{13}C$-correlated spectra; HMQ |

The $^1H$-spectrum contains signals from a main compound. The three $^1H$-signals at 4.03, 3.90 and 3.43 ppm are found to be signals from methine-groups (see HMQC). Furthermore, the obtained $^{13}C$-signals at 66.9 B 75.1 correlate to these protons, and their chemical shifts imply that the carbons are bound to oxygen, possibly as CHOH-groups. The three signals are bound to each other in a straight chain as found in the COSY spectrum.

The main compound also showed $^1H$-signals at about 1.72 B 1.99 ppm with correlations to $^{13}C$-signals at about 40 ppm. The HMQC spectrum reveals that these signals are $CH_2$-groups and the COSY spectrum implies that the individual protons in each $CH_2$-group are unequal.

Judged from the COSY spectrum, the two outer CHOH-groups are bound to different $CH_2$-groups. This gives the following partial structure:

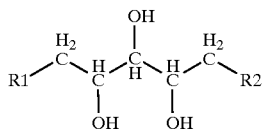

However, as many of the $^1H$—$^1H$-couplings were larger/smaller compared with normal couplings it seemed likely that the compound rotation was sterically hindered and therefore a ring system was suggested. Furthermore, as the $^{13}C$-shifts for the $CH_2$-groups were near 40 ppm it seemed likely that R1=R2=a carbon atom. This gave the following partial structure:

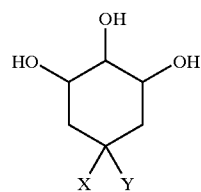

No signals that explain X and Y in the compound could be found in the NMR spectra. After the NMR spectra were obtained also MS-analysis was performed. The sample was introduced into the MS by infusion. MS spectra on the $D_2O$ solution diluted with acetonitrile (ACN) (50/50) gave the mass number of 197 (negative ions, M−D=195). Then the solution was evaporated by means of a gentle stream of nitrogen and reconstituted in $H_2O$/ACN (50/50). Here the mass number 192 was achieved (negative ions, M−H=191). In conclusion, the compound mass number is 192 and contains 5 exchangeable protons. When combining the information obtained from NMR and MS the following structure is proposed for the main compound:

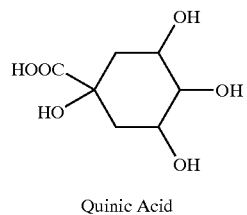

Quinic Acid

This structure is quinic acid. Reference spectra obtained using authentic quinic acid were identical to that isolated and purified from C-MED-100®.

Quinic acid, now identified as the active ingredient of C-MED-100®, is a known compound occurring as an intermediate metabolite in the natural synthesis of many aromatic compounds. (Bohm, B A, Shikimic acid (3,4,5-trihydroxy-1-cyclohexene-1-carboxylic acid), Chem. Rev. 65: 435–466, 1965). Hence, it is disclosed here that quinic acid and its analog are expected to occur in many botanical species, giving them added nutritional and health benefits.

The only known prior art disclosing any medical uses of quinic acid and its analogs is for the treatment of skin wrinkles (U.S. Pat. Nos. 5,656,665 and 5,589,505) and of flu as neuroamidase inhibitors (U.S. Pat. Nos. 6,111,132 and 6,225,341). There has been no prior art disclosure that quinic acid and its analogs might be useful in treating the disorders for which C-MED-100® has been useful such as aging, inflammation, immune suppression, and control of tumor growth and DNA repair.

Hence, this disclosure is of these additional uses for quinic acid and its analogs, especially quinic acid lactone. Moreover, quinic acid does not give a positive chemical reaction for a CAE. However, upon review of this structure, it became apparent that quinic acid might form a quinic acid lactone upon heating, which in turn would react as a CAE. (Fischer, H. O. and Dangschat, G. Helv. Chim Acta 18: 1200, 1935). Furthermore, treating the quinic acid lactone with 1% aqueous ammonia could convert it back to quinic acid. This chemistry was validated using purified quinic acid, and establishes that the active ingredient present in C-MED-100® has been synthesized during the historical medical preparation of this Cat's Claw product. Example

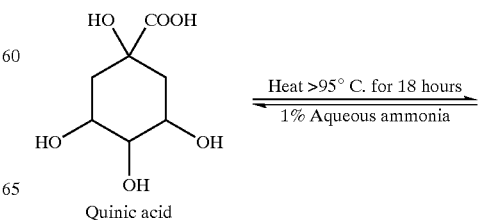

Quinic acid

-continued

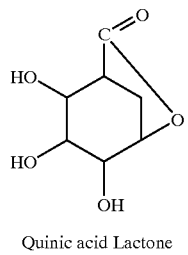

Quinic acid Lactone

EXAMPLE 3

This example exploits the biochemical knowledge presented in examples 1 and 2 to determine that the active component of C-MED-100® is in fact quinic acid lactone. C-MED-100®, quinic acid and quinic acid lactone all absorb to charcoal, and when they did both the biological activity and UV absorption at 200 nm of C-MED-100® was also removed. This data teaches that the bioactive component of C-MED-100® absorbs maximally at 200 nm. The TLC results report that there are only 2 components of C-MED-100® having such an absorption maxima. The components, located at $R_f$=0.05 and $R_f$=0.3, when chromatographed in 1% ammonia in ethanol, correspond to quinic acid and quinic acid lactone, respectively.

However, upon evaluation, the bioactive properties of the bioactive component of C-MED-100® could be almost completely accounted for by quinic acid lactone. As a result, the anti-aging, anti-inflammatory, immune and DNA repair enhancing and anti-tumor properties of C-MED-100® are due to the presence of quinic acid lactone. Those properties are hereby disclosed as attributable to quinic acid lactone.

Table 1 illustrates the relative biochemical activities of (i) the isolated bioactive component of C-MED-100®, (ii) quinic acid, and (iii) quinic acid lactone:

TABLE 1

Comparison of active ingredient of C-MED-100 ®
to quinic acid and its lactone.
(Parameters are approximations.)

| Chemical Parameter | C-MED-100 ® active ingredient | Quinic acid | Quinic acid lactone |
|---|---|---|---|
| Charcoal absorption in water | yes | yes | yes |
| $A_{UV}$ maximum in water | 200 nm | 200 nm | 200 nm |
| TLC in approximately 1% ammonia in 99% ethanol using $A_{200}$ nm for detection | $R_f$ = 0–0.05 $R_f$ = 0.2–0.3 | $R_f$ = 0–0.05 | $R_f$ = 0.2–0.3 |
| Formation of hydroxamic acid/ferric chloride color complex | yes | no | yes |
| Bioassay efficacy using $IC_{50}$ in HL-60 cells | 40 µg/ml | >3000 µg/ml | 80 µg/ml |
| Bioassay after 1% aqueous ammonia $IC_{50}$ HL-60 cells | >3000 µg/ml | >3000 µg/ml | >3000 µg/ml |

From the foregoing comparison, it is apparent that the bioactive component in C-MED-100® is, in fact, quinic acid lactone. Specifically, the relative $IC_{50}$ values for the C-MED-100® bioactive component, quinic acid, and quinic acid lactone confirm that the bioactive component cannot be quinic acid, per se, but must be an analog thereof, such as quinic acid lactone. The difference in $IC_{50}$ values for the C-MED-100® bioactive component and quinic acid lactone is not significant, and is likely due to the synergistic effect of other compounds present in C-MED-100®. However, the higher efficacy of the active ingredient, quinic acid lactone, in C-MED-100® than in its pure form indicates that the quinic acid lactone is more active in the presence of other naturally occurring components in C-MED-100® such as quinic acid.

While the invention has been described with respect to certain specific embodiments, it will be appreciated that many modifications and changes may be made by those skilled in the art without departing from the invention. It is intended, therefore, by the appended to cover all such modifications and changes as may fall within the true spirit and scope of the invention.

What is claimed is:

1. A method for enhancing the immune competency of a mammal by inhibiting TNF-α production or inducing apoptosis of white blood cells, comprising
    administering to said mammal a pharmaceutical composition comprising
        a pharmaceutically effective amount of a purified, isolated quinic acid alkyl ester having a UV absorption maximum at approximately 200 nm and a bioassay efficacy using $IC_{50}$ in HL-60 cells of less than 100 µg/ml, and
        a nontoxic inert carrier or diluent in an amount effective to inhibit TNF-α production or to induce apoptosis of white blood cells, where said administration is other than topical.

2. A method for treating disorders associated with the immune system of a mammal by inhibiting TNF-α production or inducing apoptosis of white blood cells, comprising
    administering to said mammal a pharmaceutical composition comprising
        a pharmaceutically effective amount of a purified, isolated quinic acid alkyl ester having a UV absorption maximum at approximately 200 nm and a bioassay efficacy using $IC_{50}$ in HL-60 cells of less than 100 µg/ml, and
        a nontoxic inert carrier or diluent in an amount effective to inhibit TNF-α production or to induce apoptosis of white blood cells, where said administration is other than topical.

3. A method for inhibiting the inflammatory response of a mammal by inhibiting TNF-α production or inducing apoptosis of white blood cells, comprising
    administering to said mammal a pharmaceutical composition comprising
        a pharmaceutically effective amount of a purified, isolated quinic acid alkyl ester having a UV absorption maximum at approximately 200 nm and a bioassay efficacy using $IC_{50}$ in HL-60 cells of less than 100 µg/ml, and
        a nontoxic inert carrier or diluent in an amount effective to inhibit TNF-α production or to induce apoptosis of white blood cells, where said administration is other than topical.

4. A method of treating disorders associated with the inflammatory response of a mammal by inhibiting TNF-α production or inducing apoptosis of white blood cells, comprising
    administering to said mammal a pharmaceutical composition comprising a pharmaceutically effective amount of a purified, isolated quinic acid alkyl ester having a UV absorption maximum at approximately 200 nm and a bioassay efficacy using $IC_{50}$ in HL-60 cells of less than 100 µg/ml, and a nontoxic inert carrier or diluent in an amount effective to inhibit TNF-α production or to induce apoptosis of white blood cells, where said administration is other than topical.

5. A method for enhancing the immune competency of a mammal by inhibiting TNF-α production or inducing apoptosis of white blood cells, comprising administering to said mammal a pharmaceutical composition comprising a pharmaceutically effective amount of a purified, isolated carboxy alkyl ester and a nontoxic inert carrier or diluent in an amount effective to inhibit TNF-α production or to induce apoptosis of white blood cells, where said carboxy alkyl ester is characterized by having a UV absorption maximum at approximately 200 nm, absorbs onto charcoal, and reacts with hydroxylamine and ferric chloride, and where said administration is other than topical.

6. A method for treating disorders associated with the immune system of a mammal by inhibiting TNF-α production or inducing apoptosis of white blood cells, comprising administering to said mammal a pharmaceutical composition comprising a pharmaceutically effective amount of a purified, isolated carboxy alkyl ester and a nontoxic inert carrier or diluent in an amount effective to inhibit TNF-α production or to induce apoptosis of white blood cells, where said carboxy alkyl ester is characterized by having a UV absorption maximum at approximately 200 nm, absorbs onto charcoal, and reacts with hydroxylamine and ferric chloride, and where said administration is other than topical.

7. A method for inhibiting the inflammatory response of a mammal by inhibiting TNF-α production or inducing apoptosis of white blood cells, comprising administering to said mammal a pharmaceutical composition comprising a pharmaceutically effective amount of a purified, isolated carboxy alkyl ester and a nontoxic inert carrier or diluent in an amount effective to inhibit TNF-α production or to induce apoptosis of white blood cells, where said carboxy alkyl ester is characterized by having a UV absorption maximum at approximately 200 nm, absorbs onto charcoal, and reacts with hydroxylamine and ferric chloride, and where said administration is other than topical.

8. A method of treating disorders associated with the inflammatory response of a mammal by inhibiting TNF-α production or inducing apoptosis of white blood cells, comprising administering to said mammal a pharmaceutical composition comprising a pharmaceutically effective amount of a purified, isolated carboxy alkyl ester and a nontoxic inert carrier or diluent in an amount effective to inhibit TNF-α production or to induce apoptosis of white blood cells, where said carboxy alkyl ester is characterized by having a UV absorption maximum at approximately 200 nm, absorbs onto charcoal, and reacts with hydroxylamine and ferric chloride, and where said administration is other than topical.

* * * * *